US009155489B2

(12) United States Patent
Zelinsky (10) Patent No.: US 9,155,489 B2
(45) Date of Patent: Oct. 13, 2015

(54) DEVICES FOR MODULATION OF RETINAL STIMULATION AND/OR RETINAL SIGNAL PROCESSING AND METHODS OF USE THEREOF (76) Inventor: Deborah Zelinsky, Northfield, IL (US)

( * ) Notice: Subject to any disclaimer, the term of this patent is extended or adjusted under 35 U.S.C. 154(b) by 186 days.

(21) Appl. No.: 13/542,381

(22) Filed: Jul. 5, 2012

(65) Prior Publication Data

US 2013/0012832 A1 Jan. 10, 2013

Related U.S. Application Data (60) Provisional application No. 61/504,552, filed on Jul. 5, 2011.

(51) Int. Cl.
*A61B 5/055* (2006.01)
*A61B 5/00* (2006.01)

(52) U.S. Cl.
CPC .............. *A61B 5/055* (2013.01); *A61B 5/0042* (2013.01); *A61B 5/4088* (2013.01); *A61B 5/4094* (2013.01)

(58) Field of Classification Search
CPC ...... A61B 3/00; A61B 3/0008; A61B 3/0016; A61B 3/06; A61B 3/063; A61B 3/066; A61B 3/09; A61B 3/10; A61B 5/0006; A61B 5/04004; A61B 5/55; A61B 5/0042; A61B 5/4088; A61B 5/4094
USPC .................................................. 600/300, 558
See application file for complete search history.

(56) References Cited

U.S. PATENT DOCUMENTS

| | | | | |
|---|---|---|---|---|
| 7,427,136 | B2 * | 9/2008 | Zelinsky | 351/219 |
| 8,226,574 | B2 * | 7/2012 | Whillock et al. | 600/558 |
| 8,470,790 | B2 * | 6/2013 | Pan et al. | 514/44 R |
| 8,808,195 | B2 * | 8/2014 | Tseng et al. | 600/558 |

* cited by examiner

*Primary Examiner* — Max Hindenburg
(74) *Attorney, Agent, or Firm* — K&L Gates LLP (57) ABSTRACT The present disclosure provides devices and methods for the modulation of retinal stimulation and/or retinal signal processing. Such methods may be useful for the diagnosis, treatment or prevention of a disease or disorder. The disclosed methods may comprise visual intervention by using lenses, prisms, mirrors, and/or filters (e.g., occluders) to alter the amount and/or direction of light on to the retina.

3 Claims, 2 Drawing Sheets

DEVICES FOR MODULATION OF RETINAL STIMULATION AND/OR RETINAL SIGNAL PROCESSING AND METHODS OF USE THEREOF

CROSS-REFERENCE TO RELATED APPLICATIONS

This application claims the benefit of U.S. Provisional Application No. 61/504,552, filed on Jul. 5, 2011, the disclosure of which is incorporated by reference herein in its entirety.

FIELD

The present disclosure provides devices for the modulation of retinal stimulation and/or retinal signal processing and the use of such devices for the diagnosis, treatment, or prevention of a disease or disorder.

BACKGROUND

Biomarkers are useful measurements to monitor ranges of neurological and biochemical activity. They can be used as warning signs of poor adaptation to changes in either internal or external environments. The eye is an apt structure to use for obtaining biomarkers, since it interacts with multiple systems. Light affects both chemical and neurological function in both the central and the autonomic nervous systems, and effects can be measured by eye movement changes, body changes (breathing, heart rate, etc), electrophysiological changes (brainwave testing EEG) by chemical assays (of blood, tears). For example, pupil size and response during visual scanning tasks has been touted as a potential biomarker for autism (Martineau, J., N. Hernandez, et al. (2011). "Can pupil size and pupil responses during visual scanning contribute to the diagnosis of autism spectrum disorder in children?" *J Psychiatr Res* 45(8): 1077-1082), the osmolarity in human corneal tear layer is though to possibly be a biomarker for dry eye severity (Suzuki, M., M. L. Massingale, et al. (2010). "Tear osmolarity as a biomarker for dry eye disease severity." *Invest Ophthalmol Vis Sci* 51(9): 4557-4561) and disruptions in rapid eye movement during sleep is found to correlate with amounts of stress (Mellman, T. A., V. Bustamante, et al. (2002). "REM sleep and the early development of posttraumatic stress disorder." *Am J Psychiatry* 159(10): 1696-1701).

Until 2003, it was commonly thought that the eyes had only two photoreceptors (cones and rods) and that its only purpose was to see. In 2003, a discovery was made of a third photoreceptor in the ganglion layer of the retina (rather than the photoreceptor layer). Approximately 2% of retinal ganglion cells contain melanopsin and are sensitive to changes in light. However, those cells, termed ipRGC—intrinsically photosensitive retinal ganglion cells, are not image producing cells as are the cones and rods. Such cells primary role is believed to signal light for unconscious visual reflexes, such as pupillary constriction and regulating a number of daily behavioral and physiological rhythms, collectively called circadian rhythms.

SUMMARY

The present disclosure provides devices for the modulation of retinal stimulation and/or retinal signal processing and the use of such devices for the diagnosis, treatment, or prevention of a disease or disorder.

The present disclosure is based on the novel finding that modulation/alteration of light that enters the eye (and subsequently hits the retina) may be used to effect brain pathways. Such modulation is based on and employs point to point brain mapping between the retinal pathways and the cortices (grey matter) in the brain as well as the subcortical pathways. In other words, a discrete area of the retina is mapped to a discrete area of the brain. As such, modulation of the light that hits the discrete area of the retina modulates the discrete area of the brain to which it is mapped. Thus, alteration of the light that hits the discrete area of the retina may be used to change brain function, alter chemical and neurological function and thus diagnosis malfunctions and/or treat a disease or disorder.

The present disclosure provides a method for diagnosis of a disease or disorder in a subject, comprising: activating non-visual retinal pathways in a subject's eye using one or more frequencies and/or intensities of light directed to one or more discrete areas of the subject's retina, and measuring brain activity before, during, and/or after activation of the non-visual retinal pathways. Non-visual retinal pathways include those retinal pathways that sense a light but do not transmit the light to the visual cortex to be translated to an image. Rather, the light prompts an internal change (e.g., a neurological, perceptual and/or biochemical response).

In some embodiments of each or any of the above or below mentioned embodiments, the brain activity is measured by electrodiagnositic or neuroimaging.

In some embodiments of each or any of the above or below mentioned embodiments, neuroimaging is performed via a fMRI.

In some embodiments of each or any of the above or below mentioned embodiments, the non-visual pathways are activated by the use of a light directed into one or both eyes. For example, a light may be directed to one or more discrete areas of a subject's retina and the resultant change in brain activity measured. Such a process permits a point by point mapping of an external stimulus (light) to brain activity. In further embodiments, the light may be modulated by using lenses, prisms, mirrors, and/or filters and the resultant change in brain activity measured.

In some embodiments of each or any of the above or below mentioned embodiments, brain activity is measured before (to establish a baseline) and/or after a traumatic event such as a concussion.

The present disclosure also provides a device for the diagnosis of a disease or disorder in a subject, said device comprising a set of lenses, prisms, mirrors, and/or filters operably attached to an electrodiagnositic or neuroimaging apparatus.

The present disclosure also provides a device for the diagnosis of a disease or disorder in a subject, said device comprising a set of lenses, prisms, mirrors, and/or filters operably attached to an instrument that records retinal activity.

The present disclosure also provides a device for the diagnosis and/or treatment of a disease or disorder in a subject, said device comprising a set of lenses, prisms, mirrors, and/or filters that modulates a light that enters such lenses, prisms, mirrors, and/or filters. Such modulation may include changing the frequency or intensity of light, focusing the light to one or more regions of the retina, or preventing or limiting the light from hitting one or more regions of the retina. In some embodiments, the device may take the form of a conventional pair of glasses, contact lenses, or a punctal plug. In some embodiments, the light that enters one or both eyes may be modulated. Modulation of a light directed to one or more discrete areas of the retina allows for the diagnosis and/or treatment of a disease or disorder.

The present disclosure provides a method for the treatment of a disease or disorder, said method comprising: diagnosing a subject as having a disease or disorder amenable to treatment by modulation of non-visual retinal pathways; and modulation of non-visual retinal pathways using one or more intensities and/or frequencies of light directed to one or more discrete areas of the subject's retina. Non-visual retinal pathways may be modulated (stimulated or inhibited) by using a device as disclosed herein.

In some embodiments of each or any of the above or below mentioned embodiments, the disease is an inflammatory disease, cardiovascular disease or disorder; post-traumatic brain injury; military or civilian traumatic brain injury and post concussion syndrome and post traumatic stress disorder; a sports injury; a learning disability; neurodegenerative diseases or disorders (e.g., Alzheimer's disease, Parkinson's disease, or multiple sclerosis); a seizure disorder (e.g., epilepsy); or a genetic disorder.

In some embodiments of each or any of the above or below mentioned embodiments, the modulation of non-visual retinal pathways is conducted at a selected time in a home setting.

In some embodiments of each or any of the above or below mentioned embodiments, the modulation of non-visual retinal pathways is conducted at a selected time in an institutional setting.

In some embodiments of each or any of the above or below mentioned embodiments, a subject's eye movements may also be recorded.

The present disclosure provides a method for the modulation of metabolic signaling pathways, said method comprising activating non-visual retinal pathways using one or more frequencies of light, wherein the activation of non-visual retinal pathways increases or decreases metabolic signaling pathways. Non-visual retinal pathways may be stimulated by using a device as disclosed herein.

The present disclosure provides a method for the modulation of gene expression, said method comprising activating non-visual retinal pathways using one or more frequencies of light, wherein the activation of non-visual retinal pathways increases or decreases metabolic signaling pathways.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

Figure 2:
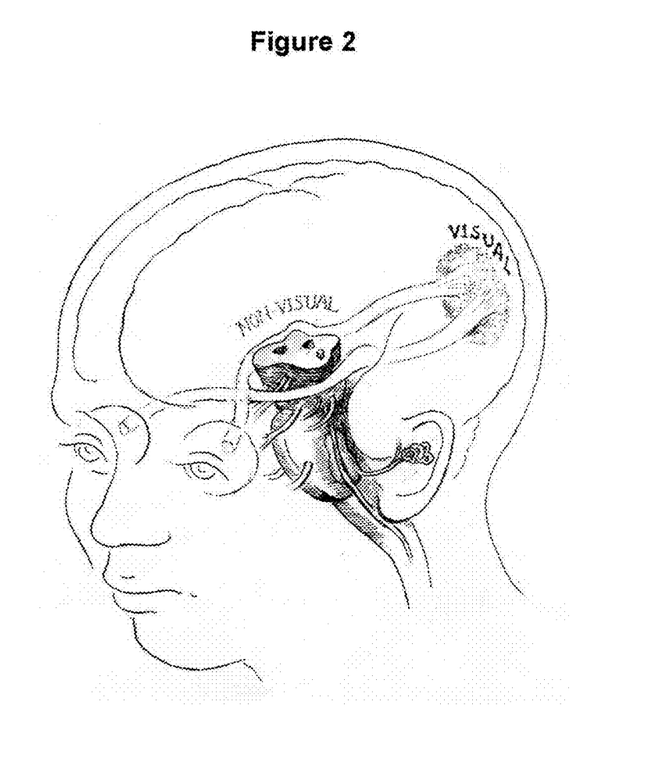
FIG. 2 shows a drawing of visual and non-visual regions of the brain that are stimulated by light that enters the eye and contacts the retina.

Traditional methods for diagnosis, treatment or prevention of diseases and/or disorders (e.g., processing difficulties, integration problems, imbalances and abnormal postures of various types) fail to address and work with the more than 160,000 peripheral retinal fibers in each eye that connect to parts of the brain and that have nothing to do with eyesight but instead are connected to the midbrain and the limbic system where all of the non-visual sensory input systems link. The inventor has surprisingly found that retinal simulation affects non-visual regions of the brain (see, FIG. 2) and is implicated in the genesis and progression of diseases and/or disorders. In other words, an external stimulation (e.g., a light entering the retina) prompts an internal change (e.g., a neurological, perceptual and/or biochemical response) which may in part lead to the manifestation of a disease or disorder. Notably, it has been discovered that modulation (e.g., activation or inhibition including a reduction) of retinal stimulation and/or retinal signal processing allows for a point of diagnostic or therapeutic intervention to diagnose, treat, or prevent diseases and/or disorders (e.g., diseases or disorders characterized by at least one retinal processing dysfunction). Such modulation may include, for example, alteration of one or more discrete areas of the retina exposed to a light, and/or changing the frequency of a light and/or the duration of time to which one or more discrete areas of the retina are exposed to a light.

Brain activity in response to a light directed to one or more discrete areas of the retina may be analyzed by any means known in the art. For example, brain activity may be measured by a fMRI that maps where local neuronal activity is by measuring the hemodynamics of blood flow or by an electroencephalogram (EEG) that maps where electrical activity occurs by measuring oscillations of brainwaves. Increased spatial and temporal resolution may be obtained by using both fMRI and EEG together. Alternatively, brain activity may be measured by analysis of retinal activity.

Conventional fMRI and EEG are restricted in that a subject is stationary and cannot move. In the instant disclosure the external environment can be altered and the patient's adaptation measured. The alterations can be done through the eye by stimulating the retina with lenses, prisms, filters, and/or mirrors. In this regard, the present disclosure also provides devices that combines a conventional fMRI or EEG machine and an instrument that can both direct a light to one or more discrete areas of a subject's retina and alter the light in one or more ways (via, lenses prisms, mirrors, and/or filters). In further embodiments, the device may be portable including hand-held.

The present disclosure also provides devices that comprises an instrument that can both direct a light to one or more discrete areas of a subject's retina and alter the light in one or more ways (via, lenses prisms, mirrors, and/or filters) and an instrument for measuring retinal activity.

The methods of the present disclosure may be used to diagnosis a disease or disorder in a subject in need thereof. Such methods may comprise activating or inhibiting non-visual retinal pathways using one or more frequencies of light, and measuring brain activity before, during, and/or after activation or inhibition of the non-visual retinal pathways. Non-visual retinal pathways include those retinal pathways that sense a light but do not transmit the light to the brain to be translated to an image. Rather, the light prompts an internal change (e.g., a neurological, perceptual and/or biochemical response).

For example, in an exemplary method of diagnosis, a light of a constant or varying frequency and/or intensity, including a filtered or refracted light, may be directed to one or more areas of the retina to map the retina and determine which areas of the brain show increased or decreased activity in response to the stimulus. Brain activity in response to stimulation of one or more areas of the retina may then be used to correlate the brain activity of subjects known to have a certain disease or disorder. For example, subjects that have post concussion syndrome exhibit a unique pattern of brain activity in response to a stimulus mapped to discrete areas of the retina. The subjects may be used to create a standard such that a subject who has brain activity that matches the standard is considered to have post concussion syndrome. As such, the identified biomarkers (unique patterns of brain activity) may be used to diagnose a disease or disorder and may provide guidance for specific therapeutic intervention. Such guidance may include the use of a pair of glasses, contact lenses, or punctual plugs specifically designed to excite or inhibit one or more areas of the retina that are associated with the unique pattern of brain activity associated with the disease or disorder.

The methods of the present disclosure may be used to treat a disease or disorder in a subject in need thereof. Such methods may comprise: diagnosing a subject as having a disease or disorder amenable to treatment by activation of non-visual retinal pathways; and activating or inhibiting non-visual retinal pathways using one or more frequencies of light. Non-visual retinal pathways may be stimulated by using a device as disclosed herein.

For example, in an exemplary method of treatment, a light of a constant or varying intensity, including a filtered or refracted light, may be focused to one or more discrete areas of the retina. Alternatively, a light may be inhibited (e.g., prevented or limited) from hitting one or more discrete areas of the retina or the light may be allowed to hit the retina for a limited duration of time. By modulating a light hitting one or more areas of the retina that are correlated with a particular disease or disorder, the disease or disorder may be treated.

The activation or inhibition of non-visual retinal pathways as described herein may also activate or inhibit visual retinal pathways.

Diseases or disorders that may be diagnosed and/or treated include, cardiovascular diseases or disorders; post-traumatic brain injury; military or civilian traumatic brain injury and post concussion syndrome and post traumatic stress disorder; sports injuries; learning disabilities; Alzheimer's disease; ALS; Parkinson's disease; multiple sclerosis; epilepsy; genetic disorders (affecting the metabolic pathways in gene expression), fibromyalgia, chronic fatigue syndrome, or Lyme's Disease.

The present disclosure also provides a syntonizer modified to direct specific wavelengths of light to one or more discrete areas of the retina. Direction of light to one or more discrete areas of the retina may be used to assess retinal loading and stress tolerance.

The present disclosure also provides methods for determining a shift in subconscious awareness into awareness or conscious attention in a subject, the method comprising contacting non-visual retinal pathways in a subject's eye using one or more increasing frequencies and/or intensities of light directed to one or more discrete areas of the subject's retina, and measuring brain activity after each tested frequency and/or intensity of light, wherein the subject is determined to shift from subconscious awareness to conscious attention where there is a change in brain activity at the one or more discrete areas of the brain mapped to the areas of the retina contacted with the light.

In some embodiments, the methods and devices provided herein may be used to determine if a subject has a traumatic brain injury including, for example, a brain injury obtained in military combat or contact athletics. In such methods, a subject's brain activity is analyzed in response to stimulus of one or more discrete areas of their retina to establish a baseline reading. After the subject is suspected of having a traumatic brain injury such as a concussion, the subject's brain activity in response to stimulus of one or more discrete areas of the retina may again be determined and compared to the prior reading to determine difference between the readings. One or more differences between the readings may indicate that the subject has a traumatic brain injury. Such differences in brain activity may include changes in brain activity known to be affected by a traumatic brain injury.

In some embodiments, the treatment methods may comprise providing a subject in need of thereof with a pair of glasses specifically designed to alter a light that hits one or more discrete areas of the retina. Such modulation may include, for example, alteration of the portion of the retina exposed to a light and/or changing the frequency of a light (including duration of time to which a subject is exposed to light) that contacts a portion of the retina. Such alteration may include changing the frequency or intensity of light, focusing the light to one or more regions of the retina, or preventing or limiting the light from hitting one or more regions of the retina.

In some embodiments, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms.

Modulation of retinal stimulation may be made by any method known in the art, including, for example, changing ambient light surrounding a subject, using glasses (or contact lenses—colored or uncolored), or using colored dye in the tears. Any of these methods may be used to affect the amount, direction, duration, and/or frequency of light entering the eye and contacting the retina.

The disease or disorder may be an inflammatory disease, cardiovascular disease or disorder; post-traumatic brain injury; military or civilian traumatic brain injury and post concussion syndrome and post traumatic stress disorder; a sports injury; a learning disability; neurodegenerative disorders (e.g., Alzheimer's disease, Parkinson's disease, or multiple sclerosis); seizure disorder (e.g., epilepsy); or a genetic disorder The present disclosure also provides devices and methods for using light to alter gene expression. In some embodiments, the device may selectively stimulate the retina in spatial and/or temporal components to alter brain function. The device may comprises a portion that alters the light (e.g., amount and/or frequency) entering the eye and a portion that records the changes in gene expression. Such a device could use any or all of the following sensory systems: proprioception, auditory or visual processing. The device may optionally exploit motor responses, brain activity or chemical content of the corneal tear layer to assess patient adaptation.

The present disclosure provides a device that uses the retina as a portal to the nervous system, so that disruptions or inefficiencies in signaling pathways could be discovered, documented and circumvented. Such a device may be free standing, hand-held or attach to a current machine, so that during brain testing, lenses and prisms and filters may be used to specifically alter retinal stimulation in space and/or time.

The present disclosure also provides a device for testing a subject's visual field. The device may take the form of a conventional visual field testing device that is further modified to comprise three lights (e.g., LEDs) of different colors including, red, blue, and green. The lights are positioned in the device such that the emitted light may be directed into a subject's eye and focused to one or more discrete areas of the subject's retina. The device may also comprise a means capable of generating a sound at a position where a light is emitted or at a position different from where the light is emitted. The device may comprise a processor programmed to control the duration that a light is illuminated, the intensity of an illuminated light, the direction of the emitted light, and/or the generation and location of a sound. Further, the processor may be programmed to illuminate one or more lights simultaneously. In some embodiments, the processor may be programmed to illuminate a light and a sound at the same position at the same time, illuminate a light and a sound at the same position at different times, illuminate a light at a first position and a sound at a second position at the same time, or illuminate a light at a first position and a sound at a second position at different times. The lights may be directed into one or both eyes and may be focused to the same or different discrete areas of the retina of one or both eyes. Such a device may be used to assess when a subject's processing shifts from lack of awareness to awareness or vice versa. For example, if a light of low intensity is directed in the right eye's nasal retinal far from fixation section and the same amount of light from the left eye's nasal retina far from fixation section, it can be determined if the subject is aware of two lights, one light or no light. Awareness of two lights, one light, or no lights is indicative of conscious brain activity in both, one, or no hemispheres of the brain. If the lights were bright on the right eye's inferior close to center and also on the left eye's superior close to center, it could be determined if the subject could perceive both at the same time. If the subject is capable of perceiving both lights at the same time, a lens could be added to the device to affect their perception until one or both of the lights appears to dim including disappear.

In some embodiments of each or any of the above or below mentioned embodiments, the methods and/or device disclosed herein are used to obtain a biomarker or monitor a subject who exhibits a biomarker indicative of a disease or disorder. For example, a biomarker may include up or down regulation of tear proteins.

The devices of the present disclosure may be useful in and applied to various settings including, for example, medicine, optometry, gaming, schools, military, and athletics. For example, when used in medicine, the device may be used in conjunction with a fMRI to determine which brain pathways are disrupted in a patient by the use of retinal stimulation. If a disease and/or disorder, such as Alzheimer's disease, in a patient can be identified in a prodromal phase, it may be treatment and/or reversed. For example, when used in optometry, the device could assess which lenses were detrimental to physiological systems, and/or which were beneficial to sensory integration, and thus stability of the systems to withstand environmental changes. For example, in gaming, the device may be used in a game designed around spatial awareness or reaction time, where the background or target sounds, colors, size, or shape might be altered or move, and a computer could track the players response. For example, in neurological classrooms, the device may be used to exemplify various neurological pathways. For example, in school, the device might be used to assess students processing For example, in hospitals; the device might be used to determine brain activity in coma patients or trauma patients (either electrical or other types of brain trauma).

Such a device may comprise a portion that attaches to a neuroimaging machine (MRI machine) and a second portion connected to earbuds to simulate virtual sounds at various locations. In some embodiments, the device may assess interactions between visual and auditory systems consisting of a computer, a set of headphones, and a recording mechanism. A patient's brain activity may then be measured. Subsequently, light would be selectively altered and changes in brain activity or motor responses recorded. The ability of the patient to adapt to changes may be assessed, in a similar manner as a cardiac stress test is used to determine comfort levels, and stress points. Data obtained from the measurement of a patient's brain activity may then be compared to data obtained from a normal patient in order to diagnose whether the patient has a specified disease or disorder.

In some embodiments, the devices of the present disclosure may be designed such that they are not operational unless the user has compensated the owner of the device for its usage.

The present disclosure also provides methods and devices for assessing a patient's processing of locating a virtual sound in space, comprising the steps of generating a sound and asking a patient to point their eyes toward the sound. Subsequently, the patient is asked again to point their eyes toward the sound when retinal stimuli is altered in one or more ways (via, lenses prisms, mirrors, and/or filters) or when the sound is altered (changing frequency, timber, volume, etc).

Point to point brain mapping from the retina to the visual cortex, allows for interventions in retinal stimulation to be used to differentiate functional pathways during fMRI testing. Such interventions can include, for example, lenses, prisms or filters, each of which alters the retinal signals in a different way. fMRI or possibly other types of studies can be used to differentiate among the three concurrent visual processing networks connected to the retina. Knowledge of those differences may enhance future research. Various clinical applications could include functional breakdowns in disease states, e.g., seizure disorders, memory deficits and visuo-cognitive abilities in patients with Alzheimer's disease and eye movement control and balance in patients with traumatic brain injuries or Parkinson's disease.

Brain Circuitry

Brain activation involves stimulation, modulation, feedback and feedforward mechanisms in two main groupings: subcortical functions and cortical processing. Each grouping is known to have multiple interconnections, with more pathways being discovered annually. These extensive feedforward and feedback systems allow for interconnectivity of individual structures as well as linkages between movements and thoughts.

Brain activity can be viewed in terms of arousal of, awareness of and attention to both the internal and the external environment. Subcortical activity, such as survival functions (circulation, digestion, respiration, etc.), remain beneath conscious awareness until altered by suprathreshold sensory stimuli, causing distracting cortical activity. An individual with a larger threshold of tolerance to sensory changes would not be burdened by those stimuli, thus allowing more efficient brain function.

Functional systems in the brain that were not in isolation (Luria, A. R. (1973). The working brain: an introduction to neuropsychology. Penguin Books). It was been proposed that the cortical brain is composed of both units and zones, which, when functioning properly, work together to regulate behaviors, senses and thinking. The units included information handling, tone and regulation of mental activity. The zones included a primary, for information gathering, a secondary, for information processing and programming, and a tertiary, for complex forms of integrated mental activity. It was hypothesized that sensation and perception were intimately involved with movement, having afferent and efferent components. It was also proposed that the eye, as an extension of the brain, is never passive, and is always actively searching to pick out essential clues from the environment. Now, almost forty years after Luria's theory was first presented, functional organization and anatomical connectivity of regions in the cerebral cortex have been documented through neuroimaging and other techniques.

In the brain, structures are grouped to accomplish specific types of tasks. For instance, in general movement networking, many interacting pathways are involved with the frontal cortices, basal ganglia and cerebellum as the "main players." The frontal cortices plan and organize movement, generating motor programs (with the prefrontal and the premotor regions contributing to different functions), the basal ganglia govern movement intention programs, and the cerebellum is involved in the coordinated adjustment (smoothing out) of movement quality. The prefrontal cortex sends voluntary commands to the basal ganglia so that appropriate movement is selected, and other cortical association areas send the basal ganglia information for acquired (automatized) movement. Sensory signals from cortical processing are sent to the matrix of the basal ganglia, while the striosomal portion of the basal ganglia attaches an "emotional valence" to that sensory information for the purpose of learning.

Fine motor tasks such as eye movements add more "players". The brainstem's oculomotor system receives direct projections from the various eyefields located in their own brain network. Frontal eye fields, parietal eye fields, prefrontal eye fields and supplementary eye fields, each have a region involved in either saccadic or smooth eye movements (Lynch, J. C. and J. R. Tian (2006). "Cortico-cortical networks and cortico-subcortical loops for the higher control of eye movements." *Prog Brain Res* 151: 461-501; Cui D. M., Yan Y. J., and Lynch, J. C. (2003). Pursuit subregion of the frontal eye field projects to the caudate nucleus in monkeys. *J of Neurophysiol*, 89: 2678-2684). Neuroanatomical studies in non-human primates determined that there are several distinct regions in the cerebral cortex (designated eye fields) forming a cortico-cortical network guiding and executing decisions for voluntary, visually guided saccadic and pursuit eye movements. Some of the subcortical structures used in eye movement, for example, involve the superior colliculus and the frontal eye fields integrating information received by the geniculate-striate pathway and contributing to more thinking and movement decisions (Ding, L. and J. I. Gold (2011). "Neural Correlates of Perceptual Decision Making before, during, and after Decision Commitment in Monkey Frontal Eye Field." *Cereb Cortex*).

Anatomical patterns of new movements, from initial learning to automation, shift over time as the movement is practiced and developed. The retention of movement schema (praxicons) is in parietal/temporal-parietal circuits and connects with the cerebellum which refines the praxicons and innervatory programs by comparing predicted movement outcome with error. These comparisons are accomplished by the brain via two types of procedures, described by theoretical control models. Forward models predict movement outcomes by projecting signals to parietal and frontal motor regions, allowing for automation and bypassing direct (slower) sensory input. Inverse cerebellar models are initiated outside of conscious awareness and bypass premotor cortex commands, allowing automatic movements. Speed and precise accuracy of intentionally guided actions and predictions is thus developed (Imamizu, H. and M. Kawato (2009). "Brain mechanisms for predictive control by switching internal models: implications for higher-order cognitive functions." *Psychol Res* 73(4): 527-544).

Movement is not in isolation from thoughts; it is one part of a network of functional circuits, each with its own pathway, synchronizing like an orchestra. Concurrent pathways form loops, including sensory stimuli, processing and motor reactions and responses. The processing can be analytical and intentional, or intuitive and habitual, leading to various brain networks, such as, visuo-spatial processing from the parietal lobe, visually guided action from the premotor cortex and navigation, imagination and planning for the future in the prefrontal cortex. (Kravitz, D. J., K. S. Saleem, et al. (2011). "A new neural framework for visuospatial processing." *Nat Rev Neurosci* 12(4): 217-230). Both the mind (cortical) and body (subcortical) systems have to adapt to continual environmental changes, at either a conscious or non-conscious level of awareness. Also, there is substantial integration between subcortical and cortical structures as well as interrelationships and interactions at micro-circuitry levels.

Figure 1:
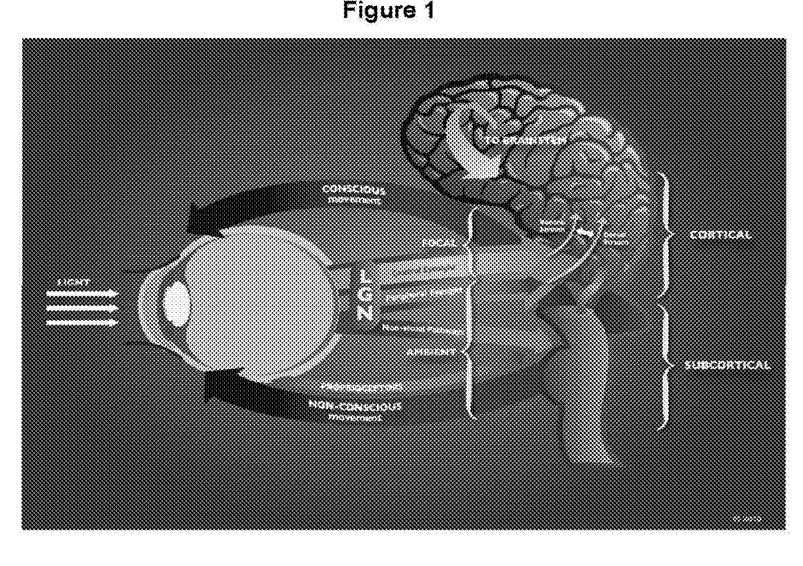
FIG. 1 shows a schematic of mechanisms believed to be involved in retinal signal processing.

At any given moment, three movement types (reflex, developed and intentional) are the result of three processing pathways, activated by different amounts of stimulation at different speeds, capturing different amounts of attention. FIG. 1 highlights the differences between how these movement types are generated. The distinctions are important because of the interrelationships among the three separate pathways. Developed movements include learned-orienting and anticipatory pathways. However, orienting movements can also be reflexive.

The present disclosure is based on the finding that it is possible during an fMRI to analyze these three processing pathways to assess which one has more of an attentional demand at the expense of the others and determine the location(s) in the brain where activity occurs. Alternatively, the present disclosure provides a tabletop or hand held machine to assess the shift in the three processing pathways without having to use a fMRI.

All cortical areas have significant inputs and major feedforward and feedback connections to numerous subcortical structures. Some functional networks share similar pathways. For instance, auditory and visual reflexive spatial orienting are controlled by a common underlying neural substrate (Santangelo, V., M. Olivetti Belardinelli, et al. (2007). "The suppression of reflexive visual and auditory orienting when attention is otherwise engaged." *J Exp Psychol Hum Percept Perform* 33(1): 137-148) and there are subspecialized areas, such as the middle temporal lobe (MT) which, in congenitally blind people, reacts to tactile motion, but in sighted people, reacts to either visual or tactile motion. (Sani, L., E. Ricciardi, et al. (2010). "Effects of Visual Experience on the Human MT+Functional Connectivity Networks: An fMRI Study of Motion Perception in Sighted and Congenitally Blind Individuals." *Front Syst Neurosci* 4: 159).

Whether the paradigm used is anatomical, physiological, psychological, neurological, etc, there is only one brain with parallel systems in action. Below are some ways to view brain activity. Each is a continuum, with a constant two-way exchange of information.

TABLE 1

Simplified continuums in brain function analysis

| | | |
|---|---|---|
| Stimulus Location | Internal | External |
| Processing Mode | Ambient Where Am I?* Ambient Where is It?* | Focal What is It* |
| Physiological Pathways | Magnocellular* Koniocellular* | Parvocellular* |
| Anatomical Categories | Subcortical | Cortical |
| Functional Networks | Survival Functions | Executive Functions |

TABLE 1-continued

Simplified continuums in brain function analysis

| Psychological Activity | Non-conscious | | Conscious | | |
|---|---|---|---|---|---|
| Perceptual Activity | | Arousal | Awareness | Attention | Intention |
| Brainwave Type | | delta | theta | alpha | beta | gamma |

Visual, auditory and somatosensory signals are transmitted partly through the thalamus and partly other subcortical regions. From the thalamus, auditory signals travel to the temporal lobe, and visual signals to the occipital lobe, later combining with proprioceptive and somatosensory information from the body in the parietal lobe for higher cortical processing (Williams, A. L. and A. T. Smith (2010). "Representation of eye position in the human parietal cortex." *J Neurophysiol* 104(4): 2169-2177).

The integration of somatosensory, auditory and visual inputs is one aspect of determining "Where am I?". There are also cognitive systems operating to assist in spatial orientation (Arthur, J. C., J. W. Philbeck, et al. (2009). "Non-sensory inputs to angular path integration." *J Vestib Res* 19(3-4): 111-125). However when using MRI machines to assess brain activity and functional circuitry in thinking and movement pathways, body movement cannot be used because it is restricted. Similarly, auditory testing is difficult to use, because there is ambient noise.

The Mind-Eye Connection: Functional Networks

Although eye movement is commonly assessed by fMRI, the complete depth of possibilities has not fully been explored. The inventor has discovered that the eye is much more than a visual sensory organ; it provides the entrance to a two-way street into the body and the mind. For the sake of simplicity, only three subsystems including, motor, sensory and attention are addressed, while remaining aware that they are part of a much bigger, more complex cortical/subcortical loop with multiple feedback and feedforward channels in a continually adapting dynamic system of metabolic and neurological functional networks.

When the classically understood visual pathway from the eye to the visual cortex is engaged in a conscious activity (i.e. seeing), it has been discovered that reflexive and responsive networks are also in use. For example, the reading process comprises not only the cortical visual activity of seeing (letters on the page), but also a concurrent process creating the foundation for visualization and interpretation. In addition, the mind is on the alert for external and internal sensory signals which may shift mental attention. If a person is reading and a loud noise occurs, attention will tend to shift as many events take place. The head reflexively turns toward the perceived sound location, postural mechanisms maintain balance and respiration, digestion and circulation systems are momentarily disrupted, to name a few. All in all, if processing is disrupted, attention is often hindered.

There are numerous factors affecting visual processing such as internal health, attention, spatial awareness, emotional state, etc., each affecting the functional networking of reflexive, intuitive (developed) and analytical (intentional) processing pathways. If there is a problem in one or more functional networks, the issue could be due to structural damage or inefficient synchronization of systems. For instance, fMRI connectivity analysis demonstrates that auditory and visual cortices are linked; altering one affects the other (Eckert, M. A., N. V. Kamdar, et al. (2008). "A cross-modal system linking primary auditory and visual cortices: evidence from intrinsic fMRI connectivity analysis." *Hum Brain Mapp* 29(7): 848-857). Recent studies propose that sensory systems might be able to be used to regulate timing of brainwaves (Hughes, J. R. (2008). "Gamma, fast, and ultrafast waves of the brain: their relationships with epilepsy and behavior." *Epilepsy Behav* 13(1): 25-31), implying that visual interventions could alter brain circuitry. fMRI testing revealed that in a resting state, activation in specific cortical networks differs between patients with Alzheimer's disease and healthy people. This distinguishing factor of decreased metabolism in certain brain structures can be a potential biomarker for Alzheimer's disease. (Greicius, M. D., G. Srivastava, et al. (2004). "Default-mode network activity distinguishes Alzheimer's disease from healthy aging: evidence from functional MRI." *Proc Natl Acad Sci USA* 101(13): 4637-4642)

Each individual has a unique filtering process that includes simultaneous and sequential processing before decisions are made as to motor output. The mind continually filters external and internal stimuli, choosing how to respond, with a complex series of conscious and non-conscious thoughts and emotions, many of which affect brain networks connected with the eye. (Reactions, on the other hand, are more automatic, occurring without those "decision-making" processes). As will be shown, each of these decisions, reactions and responses can be thought of in terms of "clues, cues and cruise control" and related to the three processing pathways. Consciously used clues lead to intentional movements, inferences of cues accessed beneath conscious awareness lead to habitual responses, and automatic reflex systems on "Cruise Control" lead to reflex movements that function unconsciously.

Those processing channels in terms of 1) movements, including eye movements, 2) sensory signal processing, including retinal signals, and 3) attentional factors, modulated by external and internal elements are described below.

Movement Networks: Reactions and Responses

There are many measurable motor outputs from the eye, including pupillary reactions, ciliary body activity, eyelid and extraocular muscles (EOM) movement. The intraocular (pupil and ciliary body) and extraocular muscles each use different circuitry (Muri, R. M., M. T. Iba-Zizen, et al. (1996). "Location of the human posterior eye field with functional magnetic resonance imaging." *J Neurol Neurosurg Psychiatry* 60(4): 445-448), often combining with feedback from eye muscle position (proprioceptors) in the eye and neck muscles.

Although the eyes can be moved voluntarily, most eye movements are reflexive (Weir, C. R. (2006). "Proprioception in extraocular muscles." *J Neuroophthalmol* 26(2): 123-127).

Reflexive reactions of extraocular muscles include the following, which share many of the same neuronal pathways:

Vestibulo-Ocular Reflex (VOR) moves the eyes to counteract head movement, allowing the eyes to maintain fixation—a function critical for stabilizing the eyes while the head is moving.

Optokinetic Nystagmus Reflex (OKN) pathways help eye stabilization during an involuntary fixation of moving objects (Swenson, R. S. (2006) Review of functional neuroscience Chapter 8D Eye movements Dartmouth medical school. Accessible at: http://www.dartmouth.edu/~rswenson/NeuroSci/chapter_8D.html).

Reflexive Saccadic eye movements—when the superior colliculus sends signals reflexively pointing the eyes to stimuli of interest, such as flashes of light or loud noises. The superior colliculus contains a spatial mapping of the external environment and receives visual, auditory and somatic sensation from many locations, including the spinal cord, the cerebral cortex and basal ganglia:

Cortical responses of extraocular muscles based on sensory input and attention include:

Non-reflexive saccadic eye movements

Vergence eye movements—convergence and divergence, aiming the eyes toward a target on the z-axis.

Smooth Pursuit eye movements—require the eyes to be fixated on a moving external target.

Fixation eye movements—maintain target in line of central eyesight.

Sensory Networks: Central and Peripheral Retinal Signals

Other neurological sensory input in the visual system includes proprioceptors from the EOM. There are also chemical pathways in the eye that have feedback and feedforward input, such as the consistency of corneal tear layer which varies as the nervous system is stressed, and the chemical gradients in the optic nerve which vary with retinal activity.

The retina itself functions constantly, extraordinarily busy with metabolic and neurological activity, even during sleep. In fact, when eyelids are closed, regardless of the waking state, photic stimulation caused by ambient lighting affects retinal (and brain) processing. Concurrently, there is non-photic stimulation from metabolic activity. Of the multiple sensory networks in the eye, this section will focus on central and peripheral retinal stimulation.

Retinal stimulation occurs in at least three ways: from extrinsic illumination (light or lack of light), from intrinsic chemical changes via circadian rhythms (Tombran-Tink, J. and C. J. Barnstable (2008). *Visual transduction and non-visual light perception*. Totowa, N.J., Humana Press), or by mechanically induced pressure. The fact that extrinsic illumination stimulates the retina, in easily manipulated ways, will help establish the visual stress biomarker proposed in the beginning of the paper. During an fMRI, the visual stress test determines when the peripheral retinal stimulation reaches its threshold and distracts central retinal attention of details. Central stimulation occurs when the macular region receives light where attention is placed.

Chemically and electrically, there is a monumental amount of internal processing occurring in the retina via the main groups of retinal cells (bipolar, ganglion, horizontal, amacrine, photoreceptor and Mueller), which are subdivided into over a hundred cell types, each performing a different task. This cellular teamwork allows for such functions as luminous efficiency, sensitivities to spectral frequencies and gated signaling channels.

Retinal processing begins at the photoreceptor level when a photon of light is absorbed by the molecule rhodopsin, converting it into an activated state. Subsequently, a cascade of chemical changes occurs in the outer retina, leading to various ion channels opening and closing, eventually eliciting an electrical response in the inner retina, which is monitored by action potentials and calcium regulation pathways. The traveling signals eventually arrive in ganglion cells, continuing through the optic nerve and into the brain (Tombran-Tink, J. and C. J. Barnstable (2008). *Visual transduction and non-visual light perception*. Totowa, N.J., Humana Press).

The superior, inferior, temporal, nasal and macular portions of the retina are developed from completely different sets of chemical pathways and genetic codes, and each of those five geographical sections in the retina is regulated by different transcription factors and develops during different timeframes (DeGrip, W. J., E. N. Pugh, et al. (2000). *Molecular mechanisms in visual transduction*. Amsterdam; New York, Elsevier; Tombran-Tink, J. and C. J. Barnstable (2008). *Visual transduction and non-visual light perception*. Totowa, N.J., Humana Press). This is important, because patterned neuronal activity in the early retina has a substantial influence on the retinotopic organization of the superior colliculus (Mrsic-Flogel, T. D., S. B. Hofer, et al. (2005). "Altered map of visual space in the superior colliculus of mice lacking early retinal waves." *J Neurosci* 25(29): 6921-6928). Therefore, stimulating selected retinal portions with visual interventions can induce processing changes.

Retinal pathways differ not only in development, but also in function. This has been demonstrated by fMRI testing indicating that nasal and temporal regions vary in melatonin suppression (Ruger, M., M. C. Gordijn, et al. (2005). "Nasal versus temporal illumination of the human retina: effects on core body temperature, melatonin, and circadian phase." *J Biol Rhythms* 20(1): 60-70). Binasal occlusion on eyeglasses has been used for years to visually treat patients with crossed eyes and brain injuries. Perhaps this occlusion alters the chemical pathways, indirectly affecting neurological circuitry in eye movement control and thus perception of surrounding space (linking motor, sensory and attentional circuitry). Processing also differs between the inferior and superior hemifields of external space (Rubin, N., K. Nakayama, et al. (1996). "Enhanced perception of illusory contours in the lower versus upper visual hemifields." *Science* 271(5249): 651-653). For instance, people are generally more attuned to visual information entering from the lower portion of external space (light coming upward stimulating the superior retina) than to light stimulating the inferior retina.

Alteration of retinal stimulation affects both subcortical and cortical processing. Visual processing has been documented in several hundred functional feedback and feedforward brain pathways encompassing almost fifty cortical regions (Klemm W R. (1996). Understanding neuroscience. St. Louis (Mo.): Mosby; p. 151-52), and fMRI allows for better three dimensional spatial resolution of these pathways. When activated by light, the retina triggers activity at three concurrent levels of processing: analytical (conscious, simultaneous or sequential), intuitive (subconscious) and autonomic (unconscious). Eventually an fMRI database of normal functions can be accumulated so that functional changes during disease processes could be compared to normed data. fMRI usage can thus aid in the differentiation of pathways in concurrent systems during mental activity.

Attentional Networks

Retinal stimulation is, of course, only one portion of sensory input to the eye. There are many other sensory signals involved, such as proprioceptor information and signals from corneal receptors. Consider the effect of a small eyelash rubbing against the cornea. During the time when the eyelash is bothersome, reflex tearing occurs, the eyelid reflexively blinks, the extraocular muscles reflexively point the eyes away from the pain, the auditory system's awareness of the surroundings constricts, the pupils change size, etc. If the person wishes to continue to see, he must apply conscious effort. In a stressed condition or diseased state, the need to apply conscious attention will occur sooner and more frequently than under normal conditions. That painful sensory stimulus creates an attentional demand, diverting attention away from the external environment and eyesight. The sensory system and motor systems are not simply mechanical; they are inextricably linked with and influenced by attentional networks.

This process of sensory input via light striking the retina does not take place in a vacuum. Other events may influence the individual's perception, including which details are selectively filtered out from the available information at a given time. The level of awareness an individual is able to experience is dependent not only on the proper functioning of the retina and other structures of the eye, but also on the availability of the mind's attentional networks—neurological and chemical. This fact offers insight into patient function and dysfunction and also presents many possibilities for designing tests to define the normal parameters of conscious attention versus reflexive and habitual activity.

Retinal reflexes changed depending on attention factors and the angle of the light (Wilson, J. A. (1911). "Retinoscopy without Atropine, and Some Observations on Ocular Headaches." *Br Med J* 2(2640): 258-259). Recently, a more analytical research project demonstrated the validity of that concept in migraine sufferers (Huang, J., X. Zong, et al. (2011). "fMRI evidence that precision ophthalmic tints reduce cortical hyperactivation in migraine." *Cephalalgia* 31(8): 925-936).

In the 1930's, Dr. A. M. Skeffington, described "vision" as an emergent concept from four intertwining circles (Where am I? Where is it? What is it? and Speech/Auditory). The "Where am I?" relies mainly on subcortical processing, the "Where is it?" "What is it" and "Speech/Auditory" rely mainly on cortical processing. Dr. Skeffington spent years promoting his thoughts that the eye was part of the body, controlled by the brain, and that changing information which entered the eye would affect the entire body (Skeffington, A. M. (1957). "The totality of vision." *Am J Optom Arch Am Acad Optom* 34(5): 241-255). This pioneering optometrist believed that sensory systems should be evaluated in total rather than in isolation. For instance, he believed that eye aiming and focusing be evaluated together as a team, termed a visual reflex, rather than separately as convergence and accommodation, since they are not separate. One responsibility of optometrists whose work emphasizes neuro-optometry is to measure the function or dysfunction of retinal circuitry. fMRI research demonstrates (decades after Dr. Skeffington's proposals) that the eyes do affect brain and body circuitry. (There is also interplay between an individual's genetic predisposition and their unique experiences, regulating brain circuitry.)

The sensory inputs of both eyes have magnocellular, koniocellular and parvocellular portions, arising from peripheral and central retinal stimulation The magnocellular portion is further divided into two smaller parts: non-conscious reflex and developed pathways. Testing the mental shift in attention from ambient processing (magnocellular pathways) to focal processing (parvocellular pathway) is important in differentiating movement pathways.

Magnocellular (M) system provides answers to "Where am I?" and "Where is It?" at a reflexive and a cortical level respectively, beneath conscious awareness, and the parvocellular (P) system answers the meaningful question of "What is It?" at the cortical level.

The fastest retinal signal pathway is the reflexive "Where am I?" portion of the magnocellular (M) pathway involving retinal signals that are processed subcortically. Of the retinal signals continuing through the optic radiations before arriving at the occipital cortex, some originate from macular stimulation (carrying information regarding color and detail) and others from peripheral retinal activation (carrying information regarding such factors as speed, location, size and shape). When entering the occipital lobe's striate cortex, the information is spatially based (externally controlled), with a point to point spatial representation of the external world mapped with pinpoint precision. However, upon exiting the occipital lobe, information is attentionally based (internally controlled), with the dorsal stream going on to the parietal lobe (carrying "Where is It?" signals of background information) and the ventral stream continuing to the temporal lobe (carrying "What is It?" signals of target information). Signals from the dorsal and ventral streams integrate, eventually arriving in the frontal lobe. From there, signals are transmitted to cranial nerves III, IV and VI which send signals to the extraocular muscles, resulting in eye movement.

In 2011, it was determined that a Koniocelluar (K) pathway activity might be gating the cortical circuits fed by the M and P pathways and hypothesized that the sensory streams can be adjusted to modify brain rhythms via parallel visual pathways (Cheong, S. K., C. Tailby, et al. (2011). "Slow intrinsic rhythm in the koniocellular visual pathway." *Proc Natl Acad Sci USA*). Also, each of the two cortical visual streams also have connections with subcortical nuclei (Webster, M. J., J. Bachevalier, et al. (1995). "Transient subcortical connections of inferior temporal areas TE and TEO in infant macaque monkeys." *J Comp Neurol* 352(2): 213-226). These studies seem to provide validity to the concept of a visual stress biomarker.

In addition to the "Where am I?" (subcortical processing), "Where is It?" (dorsal stream) and "What is It?" (ventral stream), hypotheses for When and Why pathways emerged in 2003 (Krekelberg, B. (2003). "Sound and vision." *Trends Cogn Sci* 7(7): 277-279). In 2011, a study found a "When" pathway and demonstrated its connections between the visual cortex and the temporal lobe (Naya, Y. and W. A. Suzuki (2011). "Integrating what and when across the primate medial temporal lobe." *Science* 333(6043): 773-776).

Sensory stimuli are filtered during processing, and decisions are made by the mind based on arousal, attention, awareness, emotions and memories. Conscious attention and awareness are often directed to different volumes of surrounding space which can be expanded or constricted depending on other internal and external signals, including general health and fatigue. Intra-cortical connections are responsible for routing information selectively to progressively higher and higher levels of processing. There is top-down processing from memory circuitry and bottom-up processing from retinal input, with the control of visual attention thought to be found in the pulvinar (the back section of the thalamus) (Olshausen, B. A., C. H. Anderson, et al. (1993). "A neurobiological model of visual attention and invariant pattern recognition based on dynamic routing of information." *J Neurosci* 13(11): 4700-4719). The thalamus is also responsible for mediating the interaction between attention and arousal during perceptual and cognitive tasks (Portas, C. M., G. Rees, et al. (1998). "A specific role for the thalamus in mediating the interaction of attention and arousal in humans." *J Neurosci* 18(21): 8979-8989; Saalmann, Y. B. and S. Kastner (2009). "Gain control in the visual thalamus during perception and cognition." *Curr Opin Neurobiol* 19(4): 408-414). Dr. Selwyn Super, an optometrist whose work emphasizes neuro-optometry, discusses intention as a top-down executive function with feedforward and anticipatory circuitry and attention with both top-down and bottom-up connections, competing with each other. In the case of patients with attentional neglect, where internal awareness of surrounding space or of their body is not normal, some are deemed sensory-attentional, others motor-intentional and still others as having representational deficits (Super, S. (2006). *Intention, attention, inattention & neglect*. Santa Ana, Calif., Optometric Extension Program).

It is clear that controlled, subtle continual change in retinal stimulation will eventually cause shifts in attentional demands and brain activity as signals trigger shifts from arousal to awareness to attention. This type of controlled change can be produced by optometric methods.

Optometric Changes to Functional Networks

Optometric tools, such as prisms, break light into frequencies and spatially distribute the light onto the retina. Each tool stimulates different areas of the retina, and as the eye moves, the optic flow sent to the brain is altered. By relying on the point to point brain mapping from the retina to the visual cortex as provided herein, and the non-visual pathways from the retina to other brain circuitry, visual intervention may be used to affect fMRI findings.

The visual changes could be accomplished by using combinations of lenses, prisms and filters (including occlusion) to alter entering light. The amount and direction of light input can be a controlled variable, and the patient's reactions to changing environmental stimuli can be measured to determine how well, and in what areas, the subcortical and cortical networks are interacting as well as its tipping point. Circuitry and pathways used for information processing can be identified and modified.

The visual spectrum has more to offer than eyesight alone. For instance, prisms and mirrors together are being developed to render objects invisible to the human eye (Zhang, B., Y. Luo, et al. (2011). "Macroscopic invisibility cloak for visible light." *Phys Rev Lett* 106(3): 033901), and mirrors are being used in rehabilitations in patients with neglect from brain trauma (Ramachandran, V. S. and E. L. Altschuler (2009). The use of visual feedback, in particular mirror visual feedback, in restoring brain function." *Brain* 132(Pt 7): 1693-1710).

Intentional eye movements and retinal stimulation are often used to induce changes in brain activity during fMRI testing. Equally as valuable, is an assessment of a patient's adaptation to environmental change. Disruption of mechanisms can lead to disease. If there is significant variation from a normal database, eye movements can be used during fMRIs to detect deviations in information processing, perhaps identifying disease states before structural breakdowns occur.

Visual interventions can be in many forms, each stimulating the retina in a different way.

Lenses—dispersing light toward the edges or the center of the retina. This change in light mainly alters the balance between central and peripheral circuitry by having the target and background occupy different percentages of the retinal input.

Yoked Prisms—angling light toward one edge of the retina. This initially affects the body's positional sense, because reflexive eye movements will point the eyes toward the incoming light, triggering internal postural mechanisms in the hips for stability of balance, to counteract the eye movement. Depending on the stability of the person's sense of balance, attention may be then shifted to external targets.

Non-yoked prisms—angling light toward either nasal or temporal retinal sensors. The eyes will also reflexively point toward the light, but this inward and outward movement stimulates different visual and postural mechanisms (shoulders rather than hips), pulling attention to the object location.

Vertical yoked prisms

Lateral yoked prisms

Filters—altering either spatial or temporal retinal input, thus affecting processing.

Tints—filtering out specific wavelengths of light, stimulating specific retinal cells, primarily altering internal sensations, via the autonomic nervous system.

Mirrors—make targets appear farther away than the mirror frame, creating a sensory mismatch between the central (target) and peripheral (background).

Movements, sensory inputs and attention can be considered within a broader framework of sensory integration. For instance, just because a person can hear and see does not mean he can simultaneously watch and listen to a moving target such as a teacher in a classroom. Using visual stress tolerated, as a biomarker for normal brain adjustments, will demonstrate adaptation ability (as long as the patient's individual tolerance level and overall physical and mental state is considered).

Eye stimulation can be used for both diagnostic and therapeutic purposes. When a person doesn't appropriately adapt to environmental changes, this proposed biomarker will be outside of a normal range. For instance, adaptation to specific spatial shifts in prisms led researchers to the conclusion that prism adaptation was processed in motor parts of the brain relating to action timing. Patients adapted to the prisms' spatial displacement independent of awareness of subjective timing (Tanaka, H., K. Homma, et al. (2011). "Physical delay but not subjective delay determines learning rate in prism adaptation." *Exp Brain Res* 208(2): 257-268).

EXAMPLES

Example 1

Diagnosis of a Seizure Disorder

A seizure disorder may be diagnosed by activating non-visual retinal pathways in a subject's eye using one or more frequencies of light directed to the subject's retina, and measuring brain activity before, during, and/or after activation of the non-visual retinal pathways.

In an exemplary method, a fMRI was performed on a subject suspected of having a seizure disorder. A fMRI apparatus was operably attached to a set of lenses, prisms, mirrors, and/or filters. Next, the fMRI was conducted while directing a light of a constant and/or varying intensity, including a filtered or refracted light to one or more areas of the subject's retina to map the retina and determine which areas of the brain show increased or decreased activity in response to the stimulus. Brain activity was recorded as light was directed to different discrete areas of the subject's retina. Next, the subject's brain activity was compared to a database comprising the measured brain activity (in response to a light directed to one or more discrete areas of the retina) of subjects with known diseases or disorders. The subject's brain activity matched (was similar to) the brain activity of another subject known to have had a seizure disorder. Thus, the subject was diagnosed with a seizure disorder.

Example 2

Treatment of Post-Concussive Syndrome

Post-concussive syndrome may be treated by activating non-visual retinal pathways in a subject's eye using one or more frequencies of light directed to the subject's retina.

In an exemplary method, a subject is diagnosed with post-concussive syndrome using for example the methodology described above in Example 1. Brain activity in the subject is then altered to treat the post-concussive syndrome by modulation of a light directed to one or more areas of the retina. For example, a light of a constant or varying intensity, including a filtered or refracted light, is focused to one or more discrete areas of the retina. Alternatively, a light may be prevented or limited from hitting one or more discrete areas of the retina or the light may be allowed to hit the retina for a limited duration of time. By modulating a light hitting one or more areas of the retina that are correlated with post-concussive syndrome, the post-concussive syndrome is treated.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A method for diagnosis of a disease or disorder in a subject, said method comprising:
    (a) activating or inhibiting non-visual retinal pathways in the subject's eye using one or more frequencies of light directed to one or more discrete areas of the subject's retina,
    (b) measuring brain activity before, during, and/or after activation or inhibition of the non-visual retinal pathways,
    (c) comparing the measured brain activity in step (b) to a database comprising brain activity measured from activating non-visual retinal pathways using one or more frequencies of light in subjects with known diseases or disorders, and
    (d) diagnosing the subject as having the disease or disorder where their brain activity is similar to the brain activity of a subject known to have the disease or disorder.

2. The method of claim 1, wherein the brain activity is measured by electrodiagnositic or neuroimaging.

3. The method of claim 2, wherein neuroimaging is performed via a fMRI.

* * * * *